(12) United States Patent
Heinrich et al.

(10) Patent No.: US 10,159,429 B2
(45) Date of Patent: *Dec. 25, 2018

(54) APPARATUS AND METHOD FOR THE DETECTION OF THE BODY POSITION WHILE SLEEPING

(75) Inventors: Adrienne Heinrich, Den Bosch (NL); Henriette Christine Van Vugt, Utrecht (NL); Rene Martinus Maria Derkx, Eindhoven (NL); Gary Nelson Garcia Molina, Verona, WI (US); Jia Du, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/117,385

(22) PCT Filed: May 29, 2012

(86) PCT No.: PCT/IB2012/052671
§ 371 (c)(1),
(2), (4) Date: Nov. 13, 2013

(87) PCT Pub. No.: WO2012/164482
PCT Pub. Date: Dec. 6, 2012

(65) Prior Publication Data
US 2015/0141762 A1 May 21, 2015

(30) Foreign Application Priority Data

May 30, 2011 (EP) .................................... 11305656

(51) Int. Cl.
*A61B 5/00* (2006.01)
*A61B 5/113* (2006.01)
(Continued)

(52) U.S. Cl.
CPC .......... *A61B 5/1116* (2013.01); *A61B 5/0075* (2013.01); *A61B 5/0077* (2013.01);
(Continued)

(58) Field of Classification Search
None
See application file for complete search history.

(56) References Cited

U.S. PATENT DOCUMENTS 5,107,845 A * 4/1992 Guern .................... A61B 5/113
348/143
5,197,490 A * 3/1993 Steiner et al. ................ 600/595
(Continued)

FOREIGN PATENT DOCUMENTS

EP 1645841 A1 4/2006
JP 5161613 A 6/1993
(Continued)

OTHER PUBLICATIONS

Taylor et al., Driver tracking and posture detection using low-resolution infrared sensing, Proc. IMechE vol. 221 Part D: J. Automobile Engineering, 2007.*
(Continued)

*Primary Examiner* — Carl H Layno
*Assistant Examiner* — Manolis Pahakis

(57) ABSTRACT

The invention relates to a method and an apparatus for the detection of the body position, especially while sleeping. More particularly, the invention relates to how the main body positions during sleep can be derived from the distribution of the reflection of a projected IR light from a subject's body under a blanket. Additionally, the breathing signals can be analyzed to determine the body posture.

13 Claims, 9 Drawing Sheets

(51) Int. Cl.
| | |
|---|---|
| *A61B 5/11* | (2006.01) |
| *A61B 7/00* | (2006.01) |
| *A61B 7/04* | (2006.01) |
| *G08B 21/04* | (2006.01) |

(52) U.S. Cl.
CPC ............. *A61B 5/113* (2013.01); *A61B 5/1113* (2013.01); *A61B 5/1118* (2013.01); *A61B 5/1128* (2013.01); *A61B 5/4806* (2013.01); *A61B 5/4818* (2013.01); *A61B 5/70* (2013.01); *A61B 7/003* (2013.01); *A61B 7/04* (2013.01); *A61B 2503/04* (2013.01); *G08B 21/0476* (2013.01)

(56) References Cited

U.S. PATENT DOCUMENTS

| | | | | | |
|---|---|---|---|---|---|
| 5,206,721 | A * | 4/1993 | Ashida | ................... | H04N 7/002 348/14.1 |
| 5,427,102 | A * | 6/1995 | Shimode | ............ | G01R 33/3854 128/925 |
| 5,444,786 | A * | 8/1995 | Raviv | ....................... | A61F 5/56 381/71.11 |
| 5,647,016 | A * | 7/1997 | Takeyama | ............... | H04S 7/304 340/961 |
| 5,844,996 | A * | 12/1998 | Enzmann | ............. | A61B 5/7475 381/71.11 |
| 5,914,660 | A * | 6/1999 | Mesibov et al. | ........... | 340/573.7 |
| 6,049,281 | A * | 4/2000 | Osterweil | ............ | A61B 5/1128 340/573.1 |
| 6,062,216 | A * | 5/2000 | Corn | ........................ | 128/204.23 |
| 6,219,645 | B1 * | 4/2001 | Byers | ...................... | G10L 15/02 381/91 |
| 6,256,046 | B1 * | 7/2001 | Waters | ..................... | G06F 3/011 345/473 |
| 6,492,634 | B2 * | 12/2002 | Marchitto et al. | ............ | 250/221 |
| 7,035,432 | B2 * | 4/2006 | Szuba | ........................ | 382/103 |
| 7,183,929 | B1 * | 2/2007 | Antebi | .................... | A63H 30/04 340/384.1 |
| 7,431,700 | B2 * | 10/2008 | Aoki et al. | ..................... | 600/534 |
| 7,835,529 | B2 * | 11/2010 | Hernandez | .......... | G10K 11/178 381/71.11 |
| 8,019,121 | B2 * | 9/2011 | Marks | ................... | A63F 13/245 3/245 |
| 8,264,517 | B2 * | 9/2012 | Bruno | ..................... | H04N 7/142 348/14.01 |
| 8,325,934 | B2 * | 12/2012 | Kuo | ..................... | A47C 21/003 381/66 |
| 2001/0019620 | A1 * | 9/2001 | Nagai | ................... | G06K 9/00228 382/104 |
| 2002/0030154 | A1 * | 3/2002 | Marchitto | ............. | A61B 5/113 250/221 |
| 2004/0131254 | A1 * | 7/2004 | Liang et al. | ................... | 382/181 |
| 2004/0210155 | A1 * | 10/2004 | Takemura et al. | ............ | 600/534 |
| 2005/0107722 | A1 * | 5/2005 | Ozaki | ................... | A61B 5/103 600/587 |
| 2006/0239538 | A1 * | 10/2006 | Sato et al. | .................... | 382/154 |
| 2006/0279428 | A1 * | 12/2006 | Sato | ..................... | A61B 5/0064 340/575 |
| 2007/0118054 | A1 | 5/2007 | Pinhas et al. | | |
| 2007/0156060 | A1 * | 7/2007 | Cervantes | ..................... | 600/534 |
| 2007/0289065 | A1 * | 12/2007 | Ikeda | .................. | A61B 5/6887 5/639 |
| 2008/0077020 | A1 * | 3/2008 | Young et al. | .................. | 600/484 |
| 2008/0304677 | A1 * | 12/2008 | Abolfathi | ........... | G10K 11/1788 381/71.1 |
| 2009/0022368 | A1 * | 1/2009 | Matsuoka | .............. | B60K 35/00 382/103 |
| 2009/0147965 | A1 * | 6/2009 | Kuo | .................... | A47C 21/003 381/71.6 |
| 2010/0262026 | A1 | 10/2010 | Meftah et al. | | |
| 2010/0278384 | A1 | 11/2010 | Shotton et al. | | |
| 2011/0064269 | A1 * | 3/2011 | Pai M.M | .......... | G06K 9/00691 382/103 |
| 2011/0087049 | A1 * | 4/2011 | Murakami | ........... | C07C 227/40 562/449 |
| 2011/0087079 | A1 * | 4/2011 | Aarts | ..................... | A61B 7/003 600/300 |
| 2011/0092857 | A1 * | 4/2011 | Herscovici-Cohen et al. ............ 600/586 | | |
| 2011/0098056 | A1 * | 4/2011 | Rhoads | .................. | G01C 21/20 455/456.1 |
| 2011/0141306 | A1 * | 6/2011 | Nakano | ................ | H04N 13/025 348/222.1 |
| 2011/0295083 | A1 * | 12/2011 | Doelling et al. | ............. | 600/301 |
| 2012/0142999 | A1 * | 6/2012 | Albu | .................... | A47G 9/0215 600/26 |
| 2012/0157757 | A1 * | 6/2012 | Ten Eyck et al. | .............. | 600/22 |
| 2012/0157870 | A1 * | 6/2012 | Derkx | .................... | A61B 7/003 600/529 |
| 2012/0212582 | A1 * | 8/2012 | Deutsch | .......................... | 348/46 |
| 2013/0013087 | A1 * | 1/2013 | Aliakseyeu et al. | ............ | 700/83 |
| 2013/0060100 | A1 * | 3/2013 | Wurm | .................... | A61B 7/003 600/301 |
| 2013/0128701 | A1 * | 5/2013 | Derkx | .................. | G01S 3/8036 367/129 |
| 2013/0289432 | A1 * | 10/2013 | Van Vugt et al. | ............. | 600/534 |
| 2013/0310657 | A1 * | 11/2013 | Sullivan | ............... | A61B 5/6892 600/301 |

FOREIGN PATENT DOCUMENTS

| | | | | |
|---|---|---|---|---|
| JP | 07163622 | A | 6/1995 | |
| JP | 2005066027 | A | 3/2005 | |
| JP | 2005253608 | A | 9/2005 | |
| JP | 2007327993 | A | 12/2007 | |
| JP | 2009163484 | A | 7/2009 | |
| JP | 2009183560 | A * | 8/2009 | |
| WO | WO 2008098943 | A2 * | 8/2008 | ............. A61B 5/11 |
| WO | WO 2008148172 | A1 * | 12/2008 | ............. A61B 5/113 |
| WO | 2009083017 | A1 | 7/2009 | |
| WO | WO 2011004299 | A1 * | 1/2011 | ............. A61B 7/003 |

OTHER PUBLICATIONS

Falie et al., Sleep Monitoring and Sleep Apnea Event Detection using a 3D camera, IEEE, 2010.*

Martinez et al., Breath Rate Monitoring During Sleep using Near-IR Imagery and PCA, ICPR, Nov. 2012.*

Yu et al., Multiparameter Sleep Monitoring Using a Depth Camera, J. Gabriel et al. (Eds.): BIOSTEC 2012, CCIS 357, pp. 311-325, 2013.*

Falie et al., Respiratory Motion Visualization and the Sleep Apnea Diagnosis with the Time of Flight (ToF) camera, Proceedings of the 1st WSEAS International Conference on Visualization, Imaging and Simulation (VIS'08), 2008.*

Nakajima et al., Development of real-time image sequence analysis for evaluating posture change and respiratory rate of a subject in bed, Physiol. Meas. 22 (2001).*

Nishida et al., Monitoring of Breath Sound under Daily Environment by Ceiling Dome Microphone, IEEE 2000.*

Series et al., Comparison of Snoring Measured at Home and During Polysomnographic Studies, Chest, 1993.*

Philip De Chazal, "Assessment of Sleep/Waker Patterns Using a Non-Contact Biomotion Sensor", 30th Annual International IEEE EMBS Conference, Vancouver, British Columbia, Canada, Aug. 20-24, 2008, pp. 514-517.

Yasuhiro Takemura et al, "A Respiratory Movement Monitoring System Using Fiber-Grating Vision Sensor for Diagnosing Sleep Apnea Syndrome", Optical Review, Springer, Berlin, DE, vol. 12, No. 1, Jan. 1, 2005, pp. 46-53, XP019353242, ISSN: 1349-9432, DOI: 10.1007/S10043-005-0046-6.

Enamul Roque et al, "Monitoring Body Positions and Movements During Sleep using WISPs", http://www.cs.virginia.edu/stankovic/psfiles/sleep.pdf, 2010.

De Koninck et al, "Sleep Positions in the Young Adult and Their Relationship With the Subjective Quality of Sleep", School of Psychology, University of Ottawa, 1983, pp. 52-59.

(56) References Cited

OTHER PUBLICATIONS

S. Gori et al, "Body Movements During Night Sleep in Healthy Elderly Subjects and Their Relationships With Sleep Stages" Brain Research Bulletin, vol. 63(5), 2004, pp. 393-397.
Wang et al, "A Robust Pose Matching Algorithm for Covered Body Analysis for Sleep Apnea" in Proceedings of the 8th IEEE International Conference on Bioinformatics and Bioengineering, 2008, pp. 1-7.
National Sleep Foundation, "2010 Sleep in America Poll", 2010, 70 Pages.
Wikipedia. Obstructive Sleep Apnea. http://en.wikipedia.org/wiki/sleep_apnea#obstructive_sleep_apnea, Downloaded Nov. 3, 2016, 17 Pages.
www.talkaboutsleep.com. Snoring Apnea. http://www.talkaboutsleep.com/sleep-disorders/archives/snoring_apnea_abstract53.htm, Downloaded Nov. 3, 2016, 4 Pages.

\* cited by examiner

APPARATUS AND METHOD FOR THE DETECTION OF THE BODY POSITION WHILE SLEEPING

CROSS-REFERENCE TO PRIOR APPLICATIONS

This application is the U.S. National Phase application under 35 U.S.C. § 371 of International Application No. PCT/IB2012/052671, filed on May 29, 2012, which claims the benefit of European Patent Application No. 11305656.8, filed on May 30, 2011. These applications are hereby incorporated by reference herein.

FIELD OF THE INVENTION

The invention relates to methods and apparatus for the detection of the body position, especially while sleeping. More particularly, the invention relates to how the main body positions during sleep can be derived from the distribution of the reflected IR light from the person's body under the blanket. Additionally, the breathing signal can be analyzed to determine the body posture.

BACKGROUND OF THE INVENTION

Detection of the body position while sleeping enables improved unobtrusive monitoring. When an image sensor is used as an off-body motion sensor, motion detection or estimation is typically applied to measure the activity level and replace actigraphs. When e.g. two persons share the bed (65% of the adult US population sleep together with a partner or children) the movements can be easier discerned when the body position is known. Motion detection alone is not sufficient for the shared-bed scenario since the areas of motion cannot indicate sufficiently well which motion areas belong to which subject when the two subjects lie close to each other. Motion estimation, where motion vectors are computed per image block, help, but only in cases when the two subjects do not move similarly in the border area. The body position can indicate which movements are likely to belong to one subject and which movements belong to the other subject.

Moreover, several other benefits regarding the body position information exist, particularly regarding sleep and health. These benefits are Enable more robust positional apnea detection: Obstructive sleep apnea (OSA) is the most common category of sleep-disordered breathing. In some patients with OSA, the severity of their apnea and sleep disturbance as measured by the Respiratory Disturbance Index (RDI) is twice as high or more when sleeping on their backs (the supine position) compared to sleeping on their sides (the lateral position). This is referred to as Positional Sleep Apnea ("PSA"). By contrast, patients with less or no change in their RDI related to sleeping position are said to have Nonpositional Sleep Apnea ("NSA"). A device designed based on the instant application may help treating patients diagnosed with PSA and increase their and their doctor's insight into the severity and possible progression of their disease. Many people suffering from OSA benefit from sleeping at a 30-degree elevation of the upper body or higher, as if in a recliner. This helps prevent the gravitational collapse of the airway. Lateral positions (sleeping on one's side), as opposed to supine positions (sleeping on the back) are also recommended as a treatment for sleep apnea. Indeed, the gravitational component is smaller in the lateral position than in the supine positions.

Coaching solutions: Body position may be included as a parameter and a user is coached/influenced to bias body positions leading to better sleep quality. The relationship between body position and sleep quality is recognized in the field of sleep research;

Poor sleepers spend longer on their backs with their head straight than good sleepers do;

People who sleep face downwards, on their stomach or on their side, weigh heavily on their jaws with static load, this incorrect position over years can cause symptoms such as migraine, trigeminal neuralgia, pain, hum, tension, and/or dizziness;

Sleep on one's side can ease the symptoms of apnea.

Complex solutions involving human models and pose recognition exist for detecting the body position of the sleeping person with a camera. They are, however, computationally more complex and only work with a thin blanket where the outline of the person is well visible. Further, such methods do not work for all major body positions (e.g. the distinction between on the stomach and on the back cannot be made).

US20070118054 discloses a method and a system for monitoring vital signs for the prediction and treatment of physiological ailments. In this patent application only the changes in the posture of the body are considered and are estimated from physiological signals. Methods and systems for monitoring vital signs for the prediction and treatment of physiological ailments are provided. The methods and systems disclosed may be applied to the monitoring of a broad range of physiological ailments or "episodes," including, but not limited to, asthma, hypoglycemia, coughing, edema, sleep apnea, labor, and REM sleep stages. The methods employ sensors, for example, non-contact sensors, adapted to detect vital signs, such as heart rate or respiration rate, to produce signals that can be analyzed for trends, deviations, or for comparison to prior conditions or criteria. The sensors may be positioned whereby the subject need not be viewed by a health care provider. Some methods and systems employ the use of "scores" based upon a combination of sensed vital signs or based upon a comparison of the vital signs to standard criteria.

WO2009/083017 discloses a movement detector for detecting the movement of a breathing activity. To enhance a movement detector for detecting the movement of a body breathing or heartbeat activity comprising a Doppler sensor with a microwave oscillator and at least one mixer in such a manner, that the detector is on the one hand efficient and safe with respect to a baby breathing or heartbeat detection and on the other hand a low cost solution, the sensor is performed as a sensor unit with a volume less than 100 cm and a sending energy lower than 10 mW.

U.S. Pat. No. 5,914,660 discloses a position monitor and alarm apparatus for reducing the possibility of sudden infant death syndrome. A device for reducing the possibility of sudden infant death syndrome (SIDS) as disclosed comprises a position-indicating device effectively coupled to a signal-producing circuit and attached to the clothing of the infant. The position indicating device provides signals, varying in response to prone and other positions assumed by the infant during sleep, allowing an associated alarm device to be activated in response to the infant's assuming a SIDS-dangerous prone or side-position. In one embodiment, the position of the infant can be determined by an optical sensor interacting with a reflective or other marker adhered to the infant. Gravity or pressure switches may also be used to provide position-responsive signals. A signal generated upon assumption of the SIDS-dangerous prone or side-positions is transmitted to a remote receiver located proximate the infant's care-giver whereupon an alarm is generated to indicate the need to reposition the infant. A constant low-level or intermittent maintenance signal can be produced to assure the continued and proper operation of the apparatus. An additional awakening alarm can be produced near the sleeping infant to further reduce the likelihood of a SIDS event.

US2010/0262026 discloses a method for the detection of the sleep position. The method as disclosed in US2010/0262026 uses ECG sensors at fixed positions, not fixed to the patient. The ECG signals recorded from the sensors are used to detect body position, using the variation of ECG potential over the surface of the body. The results may be processed by measuring artifacts related to the angle between the sensors and the heart, in particular the polarity of the QRS complex. The sensors may be fixed on the upper surface of a bed and used to monitor the sleep position.

SUMMARY OF THE INVENTION

It is therefore the object of the invention to provide a method as well as a device enabling a contactless detection of a body's posture, especially while sleeping.

With respect to the method, this object is achieved by a method for the detection of the posture of a body, especially while sleeping, the method comprising the steps of:
providing a bedding;
projection of a pattern of electromagnetic radiation at least on a part of said bedding;
detection of the reflection of the projected pattern caused by a body laying on said bedding;
comparing the reflection pattern with reflection pattern representing typical body postures.

The term bedding as used in this context should be understood as any kind of device enabling a subject to rest his or her body, e.g., a bed, a mattress, a deck-chair, or any other kind of lie down area, while the term subject refers to human or animal.

The phrase electromagnetic radiation refers to light at the visible wavelength, e.g. about 380 nm to about 780 nm, as well as electromagnetic radiation at a wavelength outside the range visible to the unaided human eye, e.g., IR-radiation at a wavelength within a range of about 780 nm to about 1 mm.

By comparison of a reflection pattern with reflection patterns representing typical body postures, the position of a body while sleeping can be determined in a contactless way without disturbing the subject monitored in during his or her sleep. The projection of the pattern facilitates the comparison of the detected reflection pattern with patterns representing typical body postures. The distribution of the reflected light is used to determine the body position. When the person lies flat in bed (e.g. in the prone, royal, Cyclops, Waterwings positions, see FIG. 1), the reflected intensity is more evenly distributed from the top to the lower part of the body whereas on the side, the reflected intensity is clearly higher around the middle and top (see FIG. 2 for examples) for the given light projector.

According to a preferred embodiment of the invention, for comparing the reflected pattern with the pattern representing typical body postures the person's body is virtually segmented into 6 major parts: Upper body left and right, middle part left and right, bottom part left and right, of which the sum of the present intensity is computed. Heuristics can be derived based on the location of the light projector. Basically, the reflected light has a higher intensity the smaller the distance between the light projector and the object since the light is reflected back quicker.

When the person lies flat, either on the belly or on the back, the distribution of the light is hardly altered by a person in bed compared to only the blanket pulled over the bed. However, when the person turns to one side, the upper and middle part of the body change the reflectance in the corresponding area (to larger or lower depending on from where the light is shining and which parts become occluded, due to e.g., legs pulled up, one side of the body blocking other side of the bed). This can be used to derive heuristics to determine the body position of a sleeping person.

According to a preferred embodiment of the invention, as the light source for the projection of the pattern a laser is used. The use of a laser as a light source enables a sharp projection of a pattern. Preferably, the laser operates at a wavelength which is outside the range that is visible to, or harmful for, the human eye, e.g., in the IR-wavelength range. Preferably, an IR-laser is used that operates at a wavelength of 808 nm to 1064 nm. The energy of the laser used as light source is preferably low enough to ensure avoidance of eye damage caused by laser radiation. Especially preferred, an IR-LED-laser is used as a light source.

In a further preferred embodiment of the invention, the projection of the pattern on said bedding is performed in an intermittent and/or modulated way. The projection may be performed e.g. once a minute, once every 10 second, or once a second, etc. Performing the projection of the pattern in an intermittent way can reduce discomfort caused by a permanent projection of the pattern. In another embodiment, the projection is modulated in its intensity. By doing so, discomfort caused by the projection can be reduced, too.

In another embodiment the projection is modulated in its frequency. This may reduce interferences caused by other light sources, e.g., night lights etc. Frequency modulation may be performed by using at least two different projectors, like e.g. two IR-LED-lasers emitting at different frequencies, e.g. 808 nm and 1064 nm. The at least two different projectors may project in an alternating way.

The detection of the reflection can be performed by video analysis of the pattern projected on the bedding. In a preferred embodiment of the invention, a CCD-sensor is used for the detection the reflection of the pattern. In an even more preferred embodiment of the invention, a low resolution sensor array is used for the detection of the reflection of the pattern. A low resolution sensor in this concern refers to sensors having a resolution of e.g., 125 cpi to 1375 cpi, preferably about 500 cpi, as are used in optical mouse sensors. Due to the reduced information needed for the detection of the body posture, the higher resolution image from a camera is not needed. By using low resolution sensors, the amount of data to be processed can be reduced, while also the privacy of the sleeping person can be preserved since the low resolution image disables identification of the person lying on the bedding.

According to another embodiment of the invention, additional information is used to determine the body posture more accurately. In an embodiment of the invention, acoustical information and/or information on the breathing amplitude is used to increase the accuracy of the body posture determination. When a flat body position is detected on the basis of the reflected pattern, to distinguish on the back from on the belly, the respiration analysis output can be included. The breathing characteristics extracted from a video signal are different when the person lies on the belly compared to when the person lies on the back. When the person lies on the back, the chest is free to move into open space without any large barrier blocking its movement. However, when the person is on the belly, the chest movement goes into the mattress and the amplitude perceived by the video is reduced. Empirically, 25% higher breathing amplitude is measured when a subject is on his back than on his stomach. The decline in the breathing amplitude towards the end of the 'back' sequence is assumed due to the more relaxed state of the subject with more shallow breathing (reduced air flow and chest expansion). When the side position is detected on the basis of the reflected pattern, the body orientation can be robustly determined by including audio signals from the two microphones on the right and left side of the head of the sleeping subject. The microphone with the larger breathing amplitude indicates the orientation of the head.

According to an embodiment of the invention, acoustical information is retrieved via at least two microphones positioned on both sides of the bedding. To detect the left/right position by means of the microphones, the following approach is used. After performance of a noise-reduction of each of the two microphones (one on the left side, one on the right side) by commonly known techniques, the breathing-events can be detected. This detection is done as shown in the following Algorithm 1, where input samples [k] are processed with k as the sample-index.

---
Algorithm 1 Event detection
---

Initialize $k_{nonzero} = 0$
for $k = 1, \infty$: do
  if $|x[k]| > \in$ then
    $\Delta k = k - k_{nonzero}$
    if $\Delta k > \Delta k_{low}$ and $\Delta k < \Delta k_{high}$ then
      event detection at sample index k
    end if
    $k_{nonzero} = k$
  end if
end for

---

The threshold $\Delta k_{low}$ and $\Delta k_{high}$ are adjusted as the minimum and maximum amount of samples that can occur between two breathing events. For example, one can adjust these two parameters as Fs and 6 Fs, with Fs being the sample-rate of the signal $x[k]$. The sample frequency may vary in a range of between 10 kHz and 100 kHz, preferably between 22 kHz and 96 kHz. Most preferred Fs=22050 Hz.

According to another embodiment of the invention, the orientation of the light source for the pattern projection as well as of the sensor/camera for the determination of the reflection is considered when detecting the body posture. Heuristics are derived for the main orientations of the camera/sensor and the light source with regard to the bedding (e.g., on top, from the bottom side of the bed, from the left side of bed, or from the right side of bed). Automatically, the corresponding heuristics are applied when the user inputs the estimated location of the camera/sensor and the light source with regard to the bed in a one-time installation of a system capable to perform the inventive method.

According to another embodiment of the invention, movement information which is available due to simultaneous actigraphy processing are used to render a more robust detection due to indications of position changes and relocation of grid segments on the subject's body.

In another aspect, the invention relates to an apparatus for the detection of postures of a body on a bedding, the apparatus comprising:

A projector for the projection of a pattern of electromagnetic waves on said bedding;

A detector for the detection of the reflection of the pattern projected by said projector;

A data processing means connected to the detector, said data processing means being capable to compare actual reflection detected by the detector with stored reflection patterns representing typical body postures.

According to a preferred embodiment of the invention with respect to the apparatus, the apparatus comprises at least one microphone connected to a data processing means. Even more preferred, the apparatus comprises at least two microphones, located on each side of the bedding.

In a preferred embodiment, the projector comprises a light emitting diode (LED) as an electromagnetic wave source, preferably a LED-laser emitting in the IR-range of the electromagnetic spectrum. In another preferred embodiment of the invention, the electromagnetic wave source is capable to emit in an intermittent and/or intensity modulated way.

According to another embodiment of the invention, the data processing means is connected to actuators capable to stimulate a subject to change his or her body posture. The actuators may be integrated in e.g. a pillow, a blanket, a t-shirt etc. In another embodiment, the actuator may be capable to amend the bedding, e.g. by lifting portions of the bedding.

In another embodiment, the data processing means is connected to an environment controlling means, e.g., an air condition controller, a heating installation controller, a room-light controller or the like.

In particular, the invention also relates to a system that measures Obtrusive Sleep Apnea (OSA) events, e.g., by measuring breathing by means of a camera or a microphone, a system that measures sleep quality or sleep depth, an output unit for outputting information regarding the determined sleep positions over the night, e.g., how long has the subject slept on the back or on the side.

In another aspect, the invention further relates to the use of a method and/or device as described above for the detection of physical health conditions related to the body posture during sleep, or for controlling the environmental situation in or around a bedding in dependence of the body posture. For example, the method and/or apparatus can be used for baby-pose detection to reduce SIDS, i.e., detection whether the baby is on the back or belly or side. Further, it can be used as a bed sores alarm system, i.e. detection of how long a person has been in the same position, and sounding an alarm when it is time to change the body position to reduce or prevent bed sores, or as a coaching system that uses the body position itself or the amount of body position shifting for sleep quality evaluation.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
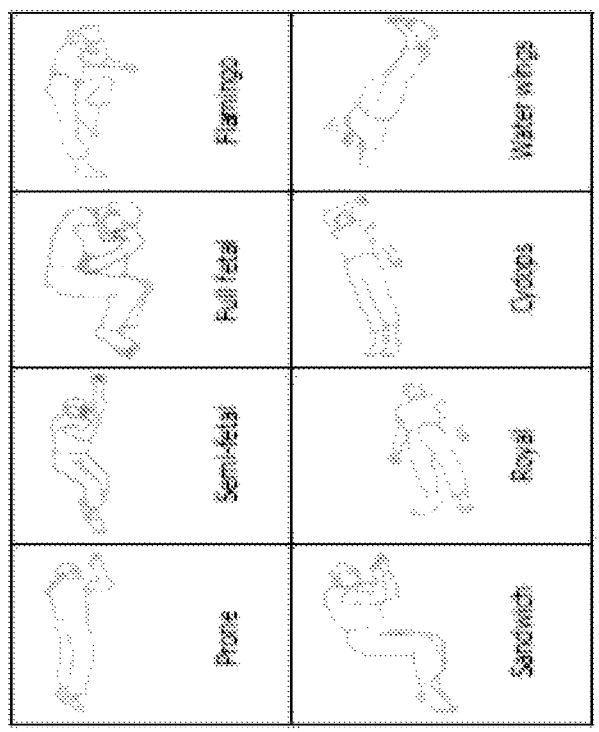
FIG. 1 shows the most common body postures for sleep (Dunkell, Samuel, "Sleep Positions," 1977)

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

FIG. 1 shows the most common body postures for sleep. Shown are the Prone, the Semi-Fetal, the Full Fetal, the Flamingo, the Sandwich, the Royal, the Cyclops, and the Water-Wings body posture. The Prone posture is lying face down with the arms extended over the head and the legs stretched out with the feet somewhat apart. The Semi-Fetal position is lying on the side with the knees drawn partway up. The Full Fetal position is lying in a folded position that obscures the face. The legs are flexed at the knees and the knees are drawn up. The Flamingo position is lying on the side with one leg straight out while the other leg is bent at the knee and flexed at a sharp angle. The Sandwich position is lying on the side with the legs placed precisely on top on one another, the thigh, knee and angle of the leg parallel to that of the other. The Royal posture is lying flat on the back. The Cyclops posture is lying flat on the back with one hand covering the eyes. In the Water-Wings posture the head rests in the palms of the hands with the elbows extended on either side.

Figure 2:
FIG. 2 shows the pattern reflection caused by different body postures at different resolution.

FIG. 2 shows a pattern reflection caused by different body postures at different resolution. In row 1 and 2 body postures are shown where the higher intensities of reflection in the middle segments are visible. These are the postures when the subject lies on the side. In row 3 images of a high and low resolution are compared. The low resolution image is sufficient for discriminating side from flat lying postures. Another possibility is to analyze the reflected light segments indicating the orientation of the legs as shown in FIG. 2. From the leg orientation, the head orientation can be directly obtained.

Figure 3:
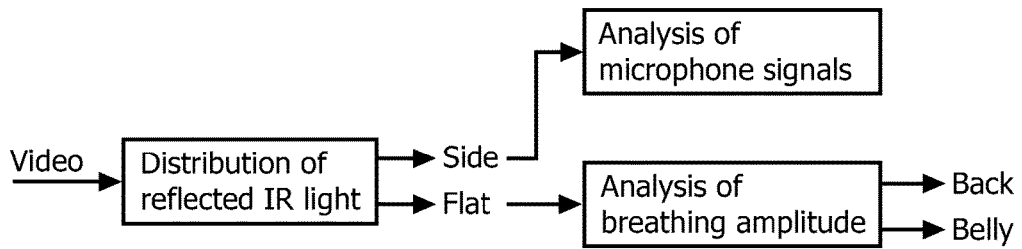
FIG. 3 shows a schematic illustration of the body posture detection according to an embodiment of the invention.

FIG. 3 shows an illustration of the body posture detection according to an embodiment of the invention. In a video signal captured from a camera the distribution of the reflected light is detected. For discriminating similar reflection pattern of flat and side postures, the audio signal coming from two microphones on either side of the bedding are taken in consideration. Further, for discriminating a back from a belly posture the breathing amplitude is taken into consideration. By analyzing the distribution of the light reflectance, the flat or side body position can be identified. When a side body position is detected, the orientation of the face can be either determined by an additional audio signal and/or by the reflected intensity distribution in the lower leg area. Adding another modality renders the system more robust. When only information on the flat or side position is needed, the images can be captured with a low resolution optical sensor, e.g. an optical mouse sensor, e.g. with a resolution of 19×19. Due to the reduced information needed by the algorithm, the higher resolution image from a camera is not needed. This is especially relevant to preserve the privacy of the sleeping person (see third row in FIG. 2). When the flat body position is detected, the breathing amplitude provides an indication on whether the subject is on the belly or on the back since the chest movement is more prominent when the sleeping subject is on his/her back. Heuristics can be derived for the main orientations of the camera/sensor and the light source(s) with regard to the bed (e.g., on the top, from the bottom side of the bed, from the left side of the bed, and/or from the right side of the bed). Automatically, the corresponding heuristics can be applied when the user inputs the estimated location of the camera/sensor and light source(s) with regard to the bed in a one-time installation.

Figure 4:
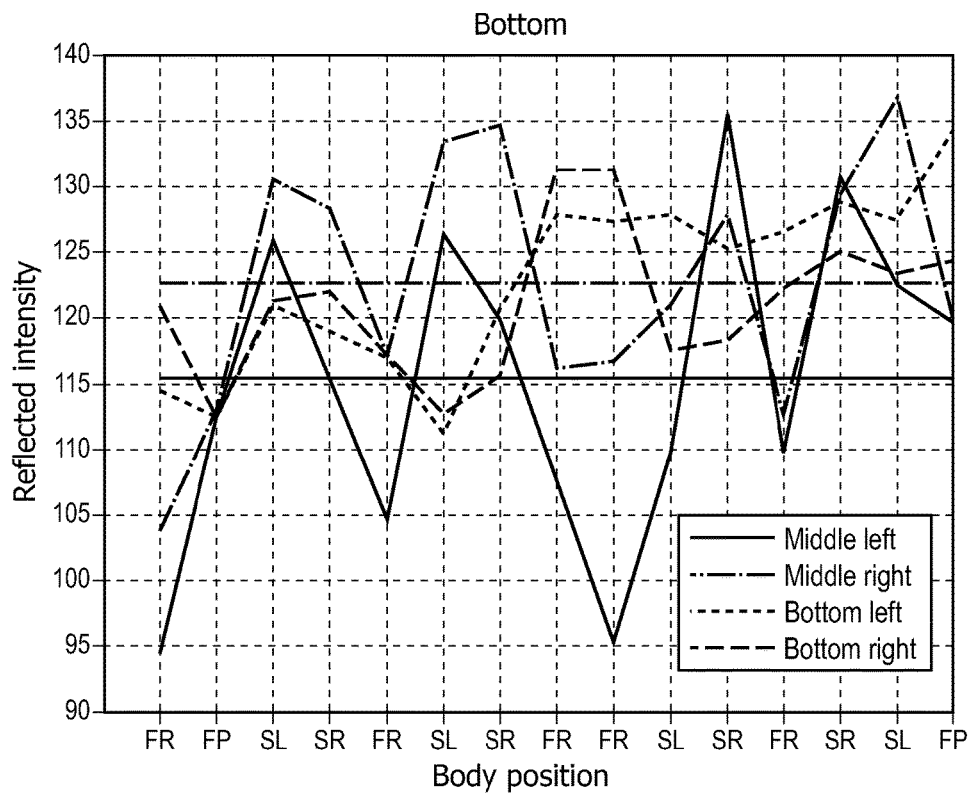
FIG. 4 shows the intensity distribution comparison of the reflection between different body postures with a light projector mounted on a wall at the lower end of the bedding.
Figure 5:
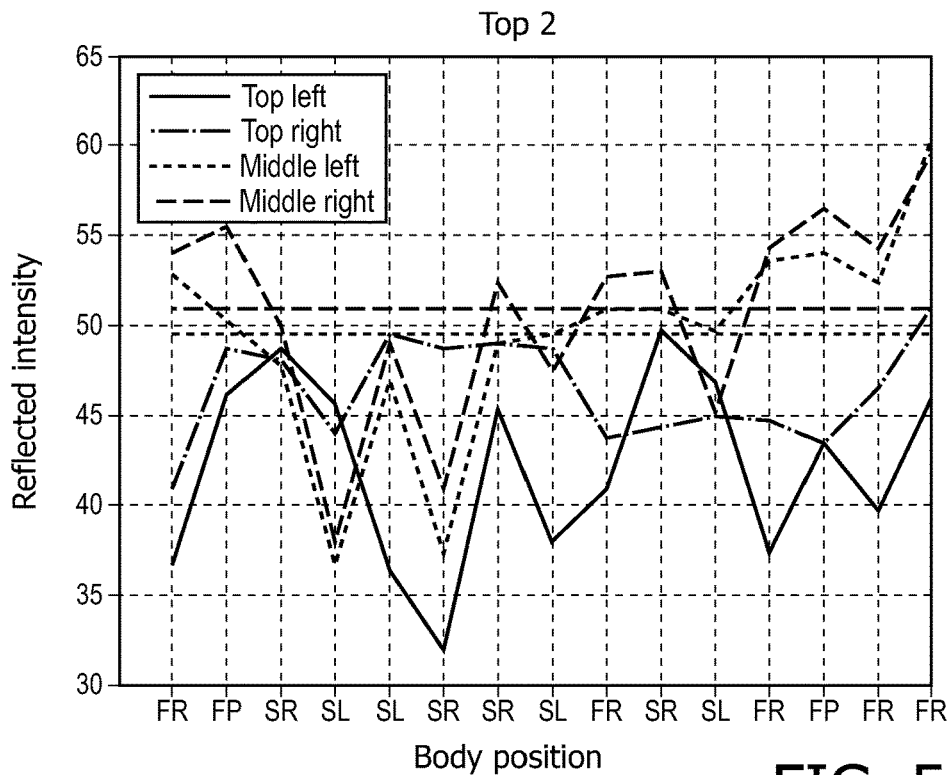
FIG. 5 shows the intensity distribution comparison of the reflection between different body postures with a light projector mounted on the ceiling above the head of a subject on the bedding.
Figure 6:
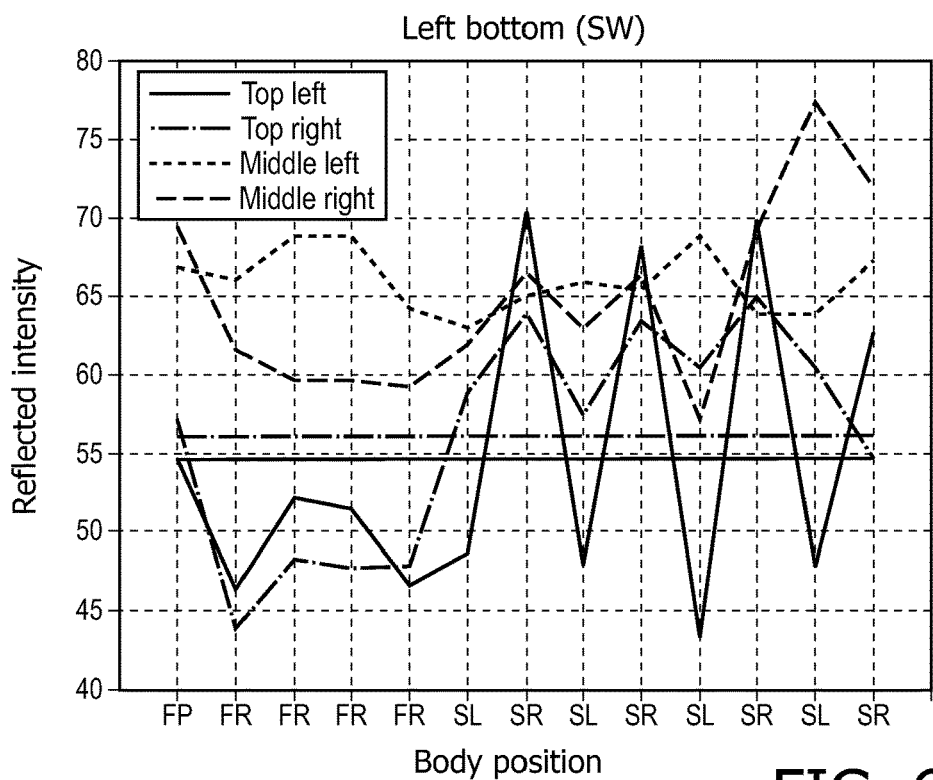
FIG. 6 shows the intensity distribution comparison of the reflection between different body postures with a light projector mounted on the left lower side of the bedding.

FIGS. 4 to 6 show the intensity distribution comparison of the reflection between different body postures for light projector positions. In the Figs. the reflection is segmented into six areas, top left/right, middle left/right, and bottom left/right, however, the reflection can be segmented into as low as two segments. For some postures, a smaller number of segments is sufficient to determine body posture. It can also be envisioned to segment the reflection into a larger number than six segments. Additionally, the grids do not need to be rectangular in order to determine a subject's body posture while sleeping. In FIGS. 4 to 6 each posture gives a specific distribution of reflection between these six segments. The distribution varies with the position of the light projector and/or the sensor/camera detecting the reflection. The following heuristics are derived for three light source locations in the bedroom (the light source is always positioned higher than the bed). As a dividing line, the "threshold" is chosen as the mean of the whole intensity curve within one segment. This could also have been done differently; it serves only as an approximate indication so that high-low intensities can be distinguished. The x-axis coding reflects flat royal (on back, FR), flat prone (on belly, FP), side right (SR), side left (SL). In total, 71 body positions with 4 different test subjects were measured. A classification accuracy of 96% correct detections and 4% false detections is achieved.

Figure 7:
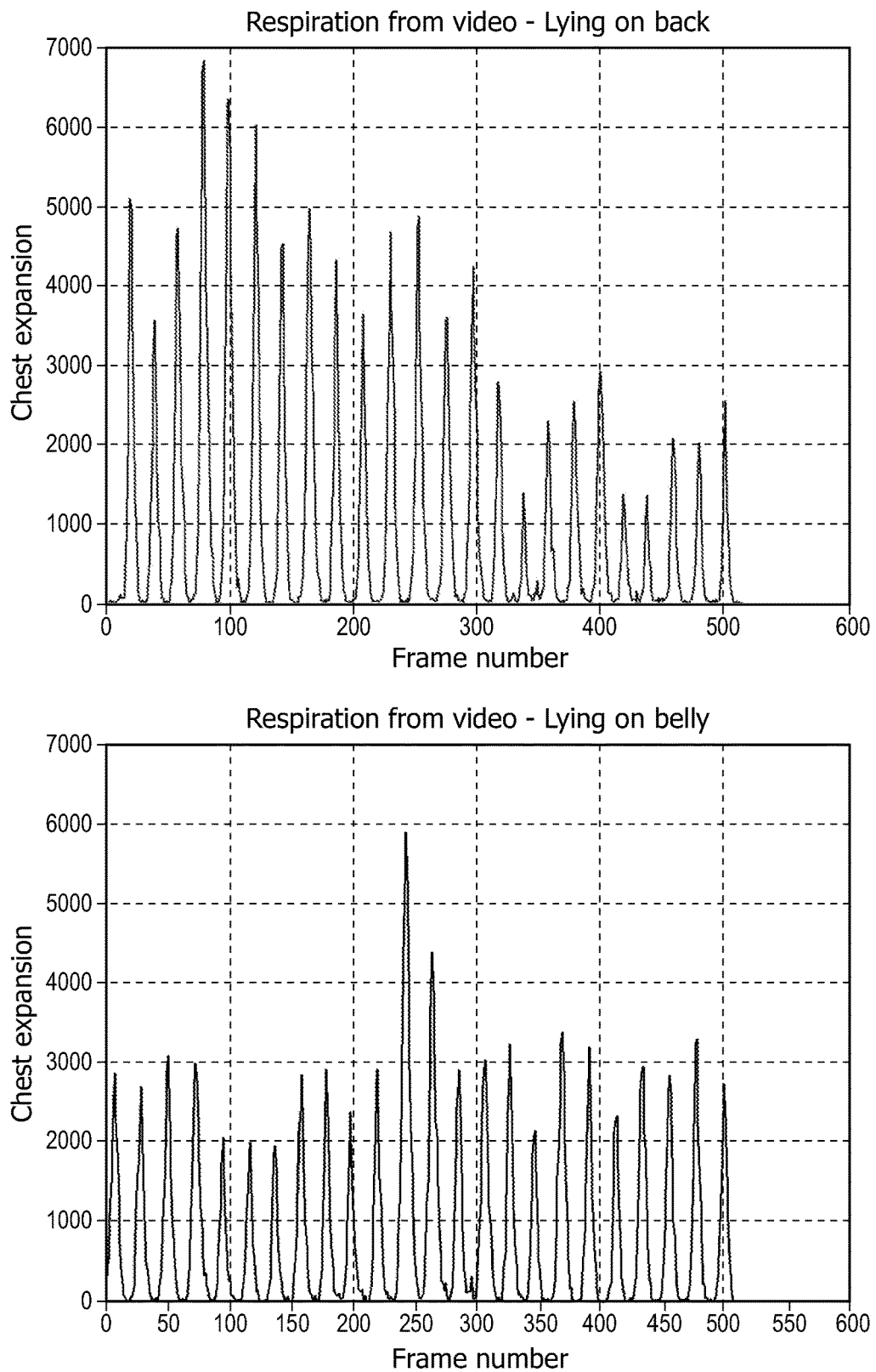
FIG. 7 shows the breathing amplitude comparison when lying on the back versus lying on the belly.

Bottom (foot part, see FIG. 4):
At least 1 middle segment high: Side
Both middle segments low: Flat
1 middle segment low, 1 middle segment close to thresh:
    If 1 bottom segment high: Side, else Flat Top (on ceiling above upper body, see FIG. 5:
At least 1 middle segment low: Side
Both middle segments high: Flat
1 middle segment close to thresh: If at least 1 top segment high: Side, else Flat Bottom left, see FIG. 6:
At least 1 top segment high: Side
Both top segments low: Flat
1 top segment low, 1 top segment close to thresh: If 1 middle segment high: Side, else Flat FIG. 7 shows the breathing amplitude comparison when lying on the back versus lying on the belly. When a flat body position is detected on the basis of the reflected pattern, to distinguish "on the back" from "on the belly," the respiration analysis output can be included. The breathing characteristics extracted from a video signal are different when the person lies on the belly compared to when the person lies on the back. When the person lies on the back the chest is free to move into open space without any large barrier blocking its movement. However, when the person is on the belly, the chest movement goes into the mattress and the amplitude perceived by the video is reduced. Empirically, a 25% higher breathing amplitude is measured when a subject is on his back. The decline in the breathing amplitude towards the end of the 'back' sequence is assumed due to the more relaxed state of the subject with more shallow breathing (reduced air flow and chest expansion).

Figure 8:
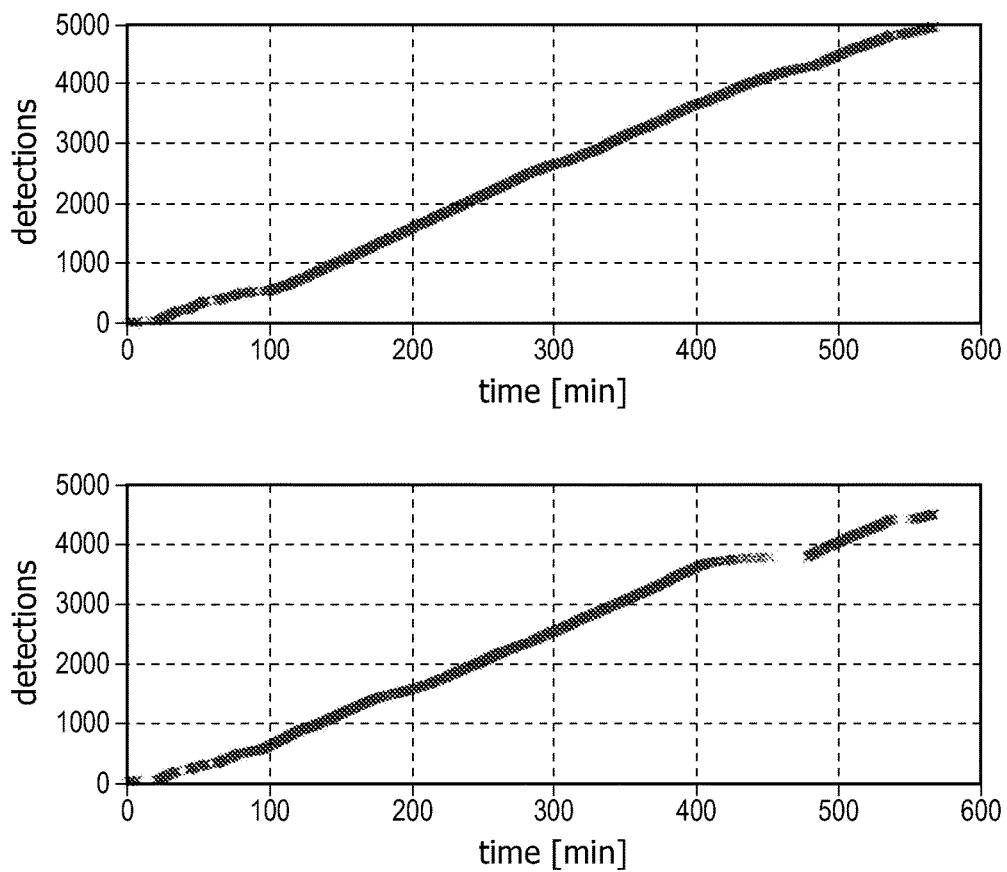
FIG. 8 shows cumulative audio events over a full-night recording of a subject.

FIG. 8 shows cumulative audio events over a full-night recording of a subject. In this plot, one can see that for each microphone there are around 5000 event detections. Clearly, it can be seen that between 400 and 500 minutes, the posture is mainly toward the left microphone. In order to more clearly detect if the breathing person lies toward the left or the right microphone, one will look at the number of detected events in an epoch of 1 minute. First, a quality measure can be computed as follows:

$$\frac{\#events(mic_{left}) - \#event(mic\_right)}{25}$$

Figure 9:
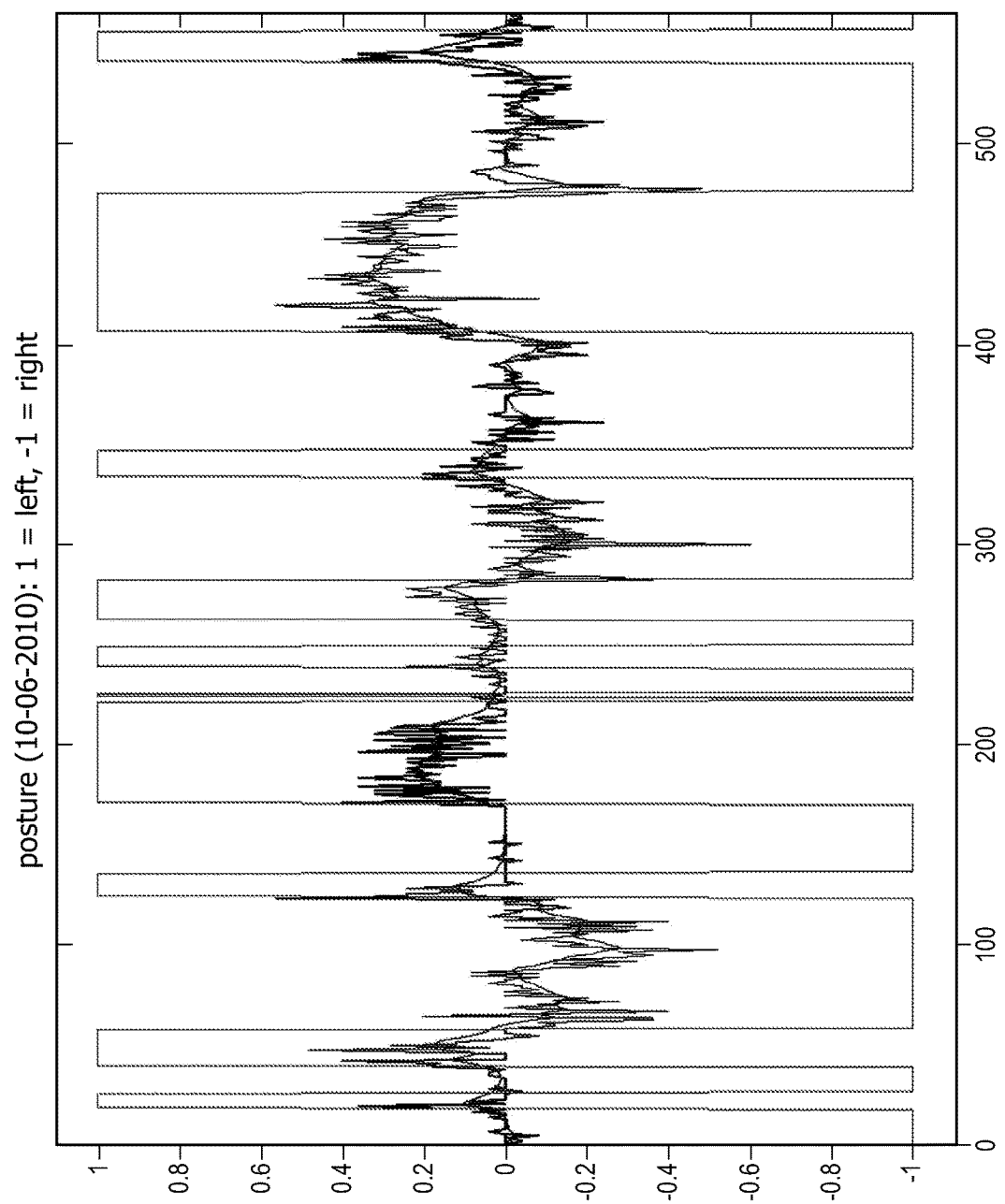
FIG. 9 shows a left/right posture estimation over a full night.

The division by 25 is chosen as one may assume that roughly 25 breaths are maximally possible during 1 minute. This measure is depicted for a full-night recording in FIG. 9. A low-pass filtering of this measure was performed to smooth the data. Finally, the low-pass filtered signal is compared with the mean level in order to detect the posture. As one can see, the posture between 400 and 500 minutes is mainly pointed toward the left microphone, 1 represents a left side posture, −1 represents a right side posture.

Example 1: Alleviation of Obtrusive Sleep Apnea (OSA)

In this embodiment, it is proposed a positional sleep apnea apparatus for monitoring the sleep position of a person, in an unobtrusive manner, comprising:
hardware: a camera that makes use of reflected light, and a microphone;
software/algorithms: for detecting the sleep position (lateral or supine), based on the images of the camera and the microphone output. Said algorithms can also include the amount of time the person is on the back or side, and the changes over the night, etc.

If OSA events are detected, the output unit can also relate these events (and the number of occurrences of the event) to the sleep positions during the night. For example:

Number of OSA events in supine position: 20
Number of OSA events in lateral position: 1.

This can be depicted visually in a graph or using text or other modality. If sleep quality or sleep depth is determined, the output unit can also relate the sleep quality or depth to the OSA events and to the body position during sleep. For example, in the lateral position, the subject's sleep quality was 30% higher than in supine position due to less OSA events. This can also be depicted visually in a graph or using text or other modality.

Figure 10:
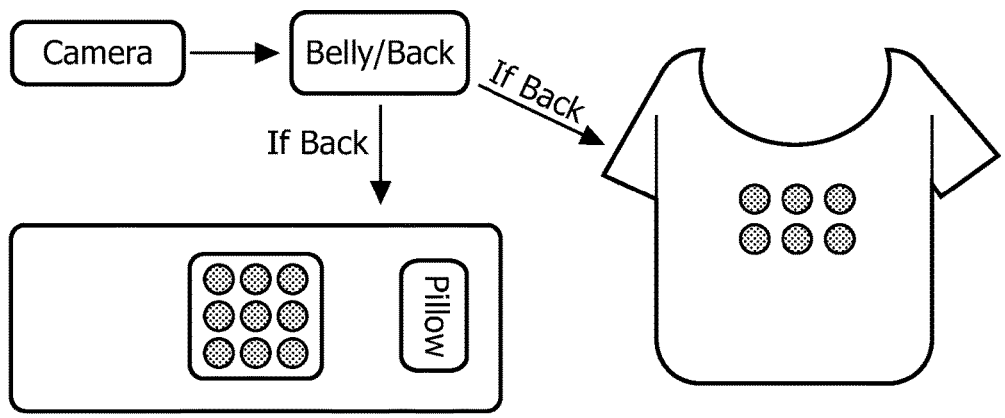
FIG. 10 shows integrated actuators usable in combination with the inventive method.
Figure 11:
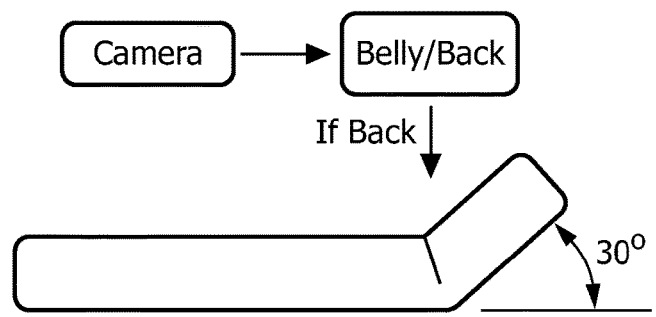
FIG. 11 shows a bed lifting device usable in combination with the inventive method.

The device can also comprise one or both of the following: an actuator to help subjects who sleep on their backs to move to sleep on their side. This can be done using tactile stimulation by, e.g., a bed that automatically lifts up or down, vibrations in the bed, a t-shirt, mattress, or pillow. The system can also behave smarter by detecting the location of a subject in bed in order to trigger certain actuators for optimum and effective turning stimulation as shown in FIG. 10 and FIG. 11. For example, the subject can be stimulated to change the body posture to one in which less OSA events occur, like e.g. the lateral body posture.

Figure 12:
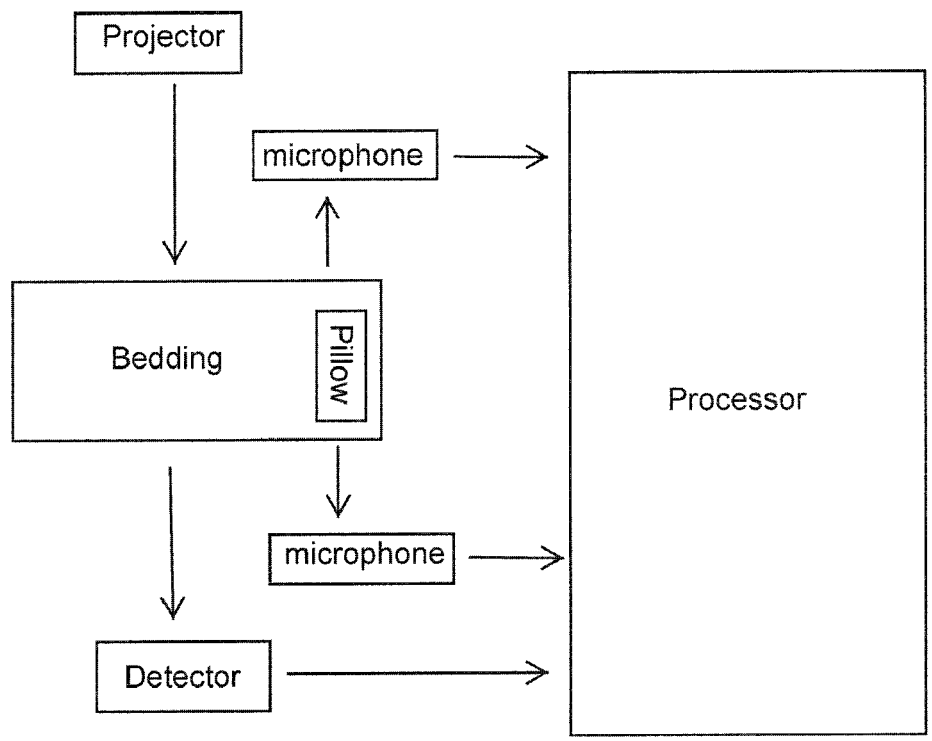
FIG. 12 shows a schematic illustration of the body posture detection apparatus according to embodiments of the present system.

FIG. 12 shows an illustration of the body posture detection apparatus according to embodiments of the present system. A projector projects electromagnetic waves on the bedding. A reflection of a pattern of the electromagnetic waves from the bedding is detected by a detector. The processor receives the reflection of the pattern such as detected as lighting intensities in embodiments of the present system by the detector for discriminating between reflection patterns based on a comparison to stored reflection patterns representing typical body postures. Further, for further discriminating between reflection patterns, the processor may also receive an audio signal coming from at least two microphones with at least one microphone positioned on each side of the bedding.

The invention claimed is:
1. A system for detection of a sleeping posture of a body on a bedding, the apparatus comprising:
a projector configured to project electromagnetic waves on at least a part of said bedding;
a low-resolution detector configured to detect a reflection of the projected electromagnetic waves;
a processor connected to the detector, said processor configured to compare a grid-based intensity distribution of the reflection of the electromagnetic waves that are detected by the detector to a plurality of stored intensity distributions of reflection patterns of electromagnetic waves to determine the sleeping posture of the body on the bedding, each of the plurality of stored reflection patterns representing a different intensity distribution of a reflection pattern due to a corresponding reference body posture of a plurality of reference body postures, wherein the processor is further configured to determine which of the plurality of reference body postures corresponds to the sleeping posture of the body on the bedding based on the comparison; and
a plurality of microphones configured to provide inputs to said processor, said processor being configured to refine the sleeping posture determined from the comparison to determine a refined posture based on the inputs from said plurality of microphones; and
wherein the processor is configured, based on the reflection detected by the detector and the inputs from said plurality of microphones, to distinguish between at least one of side and flat sleeping postures, to distinguish between left-side and right-side sleeping pos- tures, and to detect sleep apnea events and correlate the sleep apnea events to the sleeping posture.

2. The system according to claim 1, wherein the projector is either an IR laser or an LED device.

3. The system according to claim 1, wherein the plural microphones are configured to generate acoustical information for use in the determination of the refined posture by the processor.

4. The system according to claim 1, wherein the grid-based intensity distribution of the reflection of the electromagnetic waves is virtually segmented into at least two parts.

5. The system according to claim 1, wherein the detector includes a sensor array.

6. The system according to claim 1, wherein the projector is configured to produce at least one of intermittent electromagnetic radiation and modulated electromagnetic radiation.

7. The system according to claim 1, wherein the apparatus further includes a camera configured to generate a video signal.

8. The system according to claim 7, wherein the processor is further configured to enhance an accuracy of the detection of the posture of the body using breathing characteristics extracted from the video signal.

9. The system according to claim 1, wherein the processor is further configured to determine an amount of time a body posture is maintained.

10. The system according to claim 1, wherein the processor is further configured to determine a number of times a body posture is changed.

11. The system according to claim 1, wherein the processor is further configured to provide an actuation signal to actuate a temperature control device to cause a change in temperature of an environment within which the detector resides.

12. The system according to claim 1, wherein the processor is further configured to provide an actuation signal to an actuator to cause a tactile sensation to be felt on the body to influence movement of the body.

13. The system according to claim 1, wherein the plurality of reference body postures correspond to at least two of a prone, semi-fetal, full-fetal, flamingo, sandwich, royal, cyclops, and water wings posture.

* * * * *